United States Patent [19]

Stahly

[11] Patent Number: 4,935,510

[45] Date of Patent: Jun. 19, 1990

[54] THIATION PROCESS

[75] Inventor: Barbara C. Stahly, Baton Rouge, La.

[73] Assignee: Ethyl Corporation, Richmond, Va.

[21] Appl. No.: 362,866

[22] Filed: Jun. 7, 1989

[51] Int. Cl.$^5$ .......................................... C07D 267/14
[52] U.S. Cl. .................................. 540/490; 540/488; 558/23; 560/9; 560/147; 564/74; 564/78; 568/20
[58] Field of Search ................. 540/488, 490; 558/23; 560/9; 564/74, 78; 568/20

[56] References Cited

U.S. PATENT DOCUMENTS 4,439,617 3/1984 Sestanj et al. .......................... 560/39
4,592,866 6/1986 Cale ..................................... 540/490
4,663,452 5/1987 Lilje ..................................... 540/490

FOREIGN PATENT DOCUMENTS 741104 11/1943 Fed. Rep. of Germany ........ 564/74

OTHER PUBLICATIONS

Scheeren et al. "Synthesis" (1973) pp. 149–151.

Primary Examiner—Robert T. Bond
Attorney, Agent, or Firm—Patricia J. Hogan

[57] ABSTRACT

Ammonium hydroxide is used in the recovery of a thiono compound prepared by reacting an organic carbonyl compound with phosphorus pentasulfide to improve the product yield.

13 Claims, No Drawings

THIATION PROCESS

FIELD OF INVENTION

This invention relates to thiono compounds and more particularly to a process for recovering such compounds which have been prepared by the thiation of the corresponding carbonyl compounds.

BACKGROUND

As disclosed in U.S. Pat. Nos. 4,439,617 (Sestanj et al.), 4,592,866 (Cale), and 4,663,452 (Lilje), German Patent No. 741,109 (Dieterle), and Scheeren et al., *Synthesis*, 1973, pp. 149-151, it is known that carbonyl compounds can be converted to the corresponding thiono compounds by reaction with tetraphosphorus decasulfide (more commonly, though less accurately, known as phosphorus pentasulfide).

Scheeren et al. teach that the reaction rates can be increased by conducting such thiations in the presence of sodium sulfide, carbonate, or bicarbonate and a polar solvent, Dieterle discloses the use of alkaline earth carbonates and oxides in such thiations to increase yields, and Lilje teaches that both the reaction rates and yields can be improved by conducting such thiations in the presence of an alkali metal bicarbonate and a hydrocarbon diluent.

Copending application Ser. No. (Case 5865) (Stahly) and Ser. No. (Case 5956) (Stahly), filed , 1989, disclose the use of diatomaceous earth, zeolites, molecular sieves, and Group IIA metal fluorides as thiation adjuvants in carbonyl compound/phosphorus pentasulfide reactions which may be conducted in the presence or absence of a polar or non-polar diluent.

In the aforementioned thiations, as well as in other known thiations of carbonyl compounds, it has been found that the recovered yield of thiono compound is apt to vary widely for no apparent cause and that the amount of thiono compound actually obtained from the thiation reaction is therefore frequently much less than the amount present in the reaction mixture at the end of the reaction.

SUMMARY OF INVENTION

An object of this invention is to provide a novel process for recovering thiono compounds that have been prepared by reacting an organic carbonyl compound with phosphorus pentasulfide.

Another object is to provide such a process which increases the yield of product.

These and other objects are attained by conducting at least part of the recovery of the thiono compound in the presence of ammonium hydroxide.

DETAILED DESCRIPTION

The carbonyl compound that is reacted with phosphorus pentasulfide to prepare the thiono compound of the invention may be any organic carbonyl compound that is thiatable with phosphorus pentasulfide, e.g., an aliphatic, cycloaliphatic, aromatic, or heterocyclic aldehyde, ketone, amide, ester, or thioester. Such compounds, of course, are already known and include, e.g., acetaldehyde, hexaldehyde, benzaldehyde, acetone, benzophenone, 4,4'-dimethoxybenzophenone, ditolyl ketone, di-(p-dimethylaminophenyl) ketone, t-butyl p-methoxyphenyl ketone, acetophenone, xanthone, ethyl formate, ethyl acetate, methyl cyclohexanoate, methyl thioacetate, ethyl thiobenzoate, imidazolone, formamide, acetamide, propionamide, phenylacetamide, N-methyl phenylacetamide, N-(3,4-dimethoxyphenyl)acetamide, N,N-dimethylformamide, N-(p-chlorophenyl)acetamide, p-nitrobenzamide, N-phenyl-p-aminobenzamide, N-phenyl-p-dimethylaminobenzamide, saccharamide, camphorimide, methyl N-[(6-methoxy-5-trifluoromethylnaphthalenyl)-carbonyl]-N-methylaminoethanoate, 2-(2-chloroethyl)-2,3-dihydro-4-methyl-1,4-benzoxazepin-5(4H)-one, 2-(2-chloroethyl)-2,3-dihydro-4-methylpyrido[3,2-f]-1,4-oxazepin-5(4H)-one, 2-(2-chloroethyl)-2,3-dihydro-4-methylnaphth[2,3-f]-1,4-oxazepin-5(4H)-one, etc.

In a preferred embodiment of the invention, the carbonyl compound is an amide, especially an aromatic amide. In a particularly preferred embodiment, it is an alkyl or aralkyl N-[(6-alkoxy-5-trifluoromethylnaphthalenyl)carbonyl]-N-alkylaminoethanoate wherein the alkyl groups contain 1-6 carbons, such as the amidoesters of Sestanj et al., the teachings of which are incorporated herein by reference. In another particularly preferred embodiment, the carbonyl compound is an aromatic 2,3-dihydro-1,4-oxazepin-5(4H)-one such as those taught in Cale (the teachings of which are incorporated herein by reference) and including, e.g., 2-(2-haloethyl)-2,3-dihydro-1,4-benzoxazepin-5(4H)-ones, 2-(2-haloethyl)-2,3-dihydro-4-alkylpyrido[3,2-f]-1,4-oxazepin-5(4H)-ones, etc., especially those substituted with an alkyl or aralkyl group in the 4-position.

The phosphorus pentasulfide, as indicated above, is the thiating agent that is also known as tetraphosphorus decasulfide. It is preferably employed in substantially pure form and is used in at least the stoichiometric amount, generally in excess of that amount. There is no maximum to the amount that may be employed except for the maximum that might be set by economic considerations. Most commonly, the sulfide is used so as to provide at least one atom, preferably at least about two atoms, of sulfur per carbonyl group.

When a thiation adjuvant is employed in the reaction, it may be any of the adjuvants mentioned above, i.e., an alkali metal bicarbonate, sodium sulfide, sodium carbonate, an alkaline earth carbonate or oxide, a Group IIA metal fluoride, diatomaceous earth, a zeolite, or a molecular sieve, or any other known adjuvant; but it is preferably sodium bicarbonate or diatomaceous earth.

Although the reaction may be conducted in the absence of a diluent, it is generally preferred to use a diluent. When a diluent is employed, it may be a polar diluent, such as acetonitrile, tetrahydrofuran, diglyme, diethyl ether, etc. However, it is preferably a substantially inert normally liquid hydrocarbon which may be aliphatic, cycloaliphatic, or aromatic and is more preferably a hydrocarbon having a boiling point of at least about 50° C., most commonly about 50°-150° C. Hydrocarbons having higher or lower boiling points may be used if desired. However, since the significance of the boiling point is that the reaction is most conveniently conducted at the boiling point of the diluent, the use of a lower boiling hydrocarbon generally leads to a slower reaction, and the use of a hydrocarbon having too high a boiling point could lead to decomposition of the product or a starting material.

Examples of hydrocarbons that can be used as the diluent include hexane, heptane, octane, nonane, decane, cyclopentane, cyclohexane, cycloheptane, benzene, toluene, xylene, etc., as well as less easily available liquid hydrocarbons. It is generally preferred to employ an aromatic hydrocarbon, such as toluene.

The reaction is conducted by combining the aforementioned ingredients of the reaction mixture and heating them at a suitable temperature, preferably reflux temperature, until a substantial amount of the carbonyl compound has been converted to the corresponding thiono compound. The time required for the reaction varies with the particular starting materials and temperature employed but is frequently about 20-30 minutes. Yields may be improved by employing anhydrous starting materials and reaction conditions.

In a preferred embodiment of the invention, the reaction is conducted by preslurrying the phosphorus pentasulfide and any adjuvant in at least a portion of the diluent, then adding the carbonyl compound (preferably as a solution in a portion of the diluent) with agitation, and heating the reaction mixture at reflux temperature until a substantial amount of the carbonyl compound has been converted to the corresponding thiono compound. It is frequently preferred to preheat the slurry of sulfide and adjuvant to a temperature close to the boiling point of the diluent for a suitable time, e.g., about 15-45 minutes, before the carbonyl compound is added.

After completion of the reaction, the product may be recovered by conventional means except for the novel use of ammonium hydroxide during at least part of the recovery process. However, work-up is facilitated when the product is recovered by adding a demulsifier (i.e., an emulsion breaker) to the thiono compound-containing reaction mixture at a temperature at which the demulsifier is liquid, subsequently adding water, and stirring for a time sufficient to achieve adequate admixture of the reaction mixture, demulsifier, and water prior to separating an organic phase and evaporating it to isolate the product. The demulsifier may be any material capable of changing the surface tension but is most suitably an alcohol, e.g., ethanol, or an ether, e.g., tetrahydrofuran, or diatomaceous earth. The best conditions for this procedure vary with the particular reaction mixture being worked up. However, in the case of an aromatic 2,3-dihydro-1,4-oxazepine-5(4H)-thione that has been prepared in toluene, it has been found that excellent results are obtained by cooling the reaction mixture to the boiling point of the demulsifier (e.g., tetrahydrofuran), adding about two parts by weight of demulsifier for each part of carbonyl compound that was used initially, cooling to room temperature, adding about one part by weight of water for each part of the initial carbonyl compound, and stirring for about 1-3 hours before separating out the various ingredients of the reaction mixture.

In the practice of the invention, ammonium hydroxide is present during at least part of the recovery process to increase the yield of product. The amount of ammonium hydroxide employed does not appear to be critical, but it is generally desirable to use at least enough to solvate most of the solids, usually at least about 0.1 equivalent based on the amount of starting material.

The ammonium hydroxide may be added to the reaction mixture from which the thiono compound is to be recovered at the beginning of the recovery step or after a portion of the thiono compound has been recovered or at least separated into a different phase from the residual solids. Thus, e.g., the ammonium hydroxide may be added to the reaction mixture resulting from the thiation reaction, after which the resultant mixture is stirred until the solids are dissolved, and the thiono compound is then extracted with an organic solvent, such as one of the aromatic hydrocarbons mentioned above as being suitable for use as diluents in the reaction. Alternatively, the major amount of the thiono compound may be separated from residual solids by extraction with an organic solvent, and, optionally after the solvent containing the dissolved thiono compound has been isolated, the ammonium hydroxide is then added, the resultant mixture is stirred until the solids are dissolved, and thiono compound is then selectively extracted from the solids in the aqueous phase with an organic solvent.

As indicated above, the ammonium hydroxide is maintained in contact with the reaction mixture or with the residual solids portion of the reaction mixture until the solids are dissolved. This ordinarily takes only about an hour at ambient temperatures, although somewhat longer times are sometimes required. If desired, the process of dissolution may be expedited by using elevated temperatures, e.g., reflux temperatures.

The invention is advantageous in that it permits the product yield to be increased in the thiation of organic carbonyl compounds with phosphorus pentasulfide.

The following examples are given to illustrate the invention and are not intended as a limitation thereof. In these examples the expression "phosphorus pentasulfide" is used to denote the commercially-available reagent having the formula $P_4S_{10}$ and usually containing significant levels of $P_4S_9$, "Amide" is used to denote 2-(2-chloroethyl)-2,3-dihydro-4-methylpyrido[3,2-f]-1,4-oxazepin-5-(4H)-one, and the "desired thioamide" refers to the thione corresponding to the Amide.

EXAMPLE I

Part A

A suitable reaction vessel was charged with a mixture of 20 mL of toluene, 1.03 g (2.32 mmol) of phosphorus pentasulfide, and 1.94 g (23.1 mmol) of sodium bicarbonate, after which the mixture was stirred slowly and heated at reflux for 30 minutes. A solution of 1.77 g (7.35 mmol) of Amide in 28 mL of toluene was then added dropwise over a period of 20-30 minutes while maintaining reflux, and refluxing was continued for an additional 20 minutes. TLC analysis showed complete conversion of Amide to the desired thioamide.

Part B

The reaction mixture resulting from Part A was allowed to cool to 80° C., treated sequentially with 3.44 g of tetrahydrofuran and 1.72 g of aqueous 5% sodium carbonate solution, and stirred overnight at ambient temperature. The toluene product solution was decanted from residual solids. The solids were washed with two 5 mL portions of toluene, and the washes and product solution were combined. HPLC analysis of the resultant 50.6 g of solution indicated that it contained 2.92% by weight of the desired thioamide, i.e., 1.48 g (5.76 mmol), a 78% yield.

Part C

The residual solids from Part B were treated with 15 mL of concentrated ammonium hydroxide, stirred at ambient temperature for one hour, and extracted with two 15 mL portions of toluene. HPLC analysis of the combined toluene phases (26.0 g) showed 0.73% by weight of the desired thioamide, i.e., 0.19 g (0.74 mmol), a 10% yield. Thus, the total yield was 88%.

EXAMPLE II

Part A

Example I, Part A, was repeated except that the ingredients of the reaction mixture were 20 mL of toluene, 1.05 g (2.36 mmol) of phosphorus pentasulfide, 1.98 g of diatomaceous earth, and a solution of 1.8 g (7.5 mmol) of Amide in 29 mL of toluene.

Part B

The reaction mixture resulting from Part A was treated as in Example I, Part B, except that the amounts of tetrahydrofuran and aqueous 5% sodium carbonate solution employed were 3.52 g and 1.76 g, respectively. The product solution resulting from this primary workup scheme weighed 57.6 g and contained 2.31% by weight of the desired thioamide, i.e., 1.33 g (5.18 mmol), a 69% yield.

Part C

The residual solids from Part B were treated as in Example I, Part C. The resultant product solution weighed 23.1 g and contained 1.99% by weight of the desired thioamide, i.e., 0.46 g (1.8 mmol), a 24% yield. Thus, the total yield was 93%.

It is obvious that many variations may be made in the products and processes set forth above without departing from the spirit and scope of this invention.

What is claimed is:

1. In a process for preparing a thiono compound by reacting an organic carbonyl compound with phosphorus pentasulfide and recovering the product, the improvement which comprises conducting at least part of the recovery in the presence of ammonium hydroxide to improve the yield of the product.

2. The process of claim 1 wherein the organic carbonyl compound is an amide.

3. The process of claim 2 wherein the amide is an aromatic amide.

4. The process of claim 3 wherein the aromatic amide is an aromatic 2,3-dihydro-1,4-oxazepin-5(4H)-one.

5. The process of claim 4 wherein the aromatic amide is 2-(2-chloroethyl)-2,3-dihydro-4-methylpyrido[3,2-f]-1,4-oxazepin-5(4H)-one.

6. The process of claim 3 wherein the aromatic amide is an N-[(6-alkoxy-5-trifluoromethylnaphthalenyl)carbonyl]-N-alkylaminoethanoate ester.

7. The process of claim 1 wherein the synthesis of the thiono compound is conducted in the presence of a thiation adjuvant.

8. The process of claim 7 wherein the thiation adjuvant is an alkali metal bicarbonate.

9. The process of claim 8 wherein the alkali metal bicarbonate is sodium bicarbonate.

10. The process of claim 7 wherein the thiation adjuvant is diatomaceous earth.

11. The process of claim wherein the amount of ammonium hydroxide employed is at least enough to solvate most of the solids.

12. The process of claim 1 wherein the product is recovered by adding ammonium hydroxide to the reaction mixture, stirring the resultant mixture until the solids are dissolved, and selectively extracting the thiono compound with an organic solvent.

13. The process of claim 1 wherein the product is recovered by separating the major amount of the thiono compound from residual solids by extraction with an organic solvent, adding ammonium hydroxide to the residual solids, stirring the resultant mixture until the solids are dissolved, and selectively extracting thiono compound from the solids in the aqueous phase with an organic solvent.

* * * * *